United States Patent
Buttle et al.

(10) Patent No.: US 7,876,096 B2
(45) Date of Patent: Jan. 25, 2011

(54) DETECTING FAILURES IN FLEXIBLE MULTISTRAND STEEL STRUCTURES

(75) Inventors: David John Buttle, Wantage (GB); William Dalzell, Winchester (GB)

(73) Assignee: MAPS Technology Limited, Oxfordshire (GB)

( * ) Notice: Subject to any disclaimer, the term of this patent is extended or adjusted under 35 U.S.C. 154(b) by 617 days.

(21) Appl. No.: 11/722,710

(22) PCT Filed: Dec. 14, 2005

(86) PCT No.: PCT/GB2005/050248

§ 371 (c)(1), (2), (4) Date: Mar. 18, 2008

(87) PCT Pub. No.: WO2006/067524

PCT Pub. Date: Jun. 29, 2006

(65) Prior Publication Data

US 2009/0015249 A1  Jan. 15, 2009

(30) Foreign Application Priority Data

Dec. 23, 2004 (GB) ................................ 0428138.2

(51) Int. Cl.
*G01N 27/82* (2006.01)
(52) U.S. Cl. .................. 324/240; 324/232; 324/220
(58) Field of Classification Search ............. 324/220, 324/240
See application file for complete search history.

(56) References Cited

U.S. PATENT DOCUMENTS

| | | | | |
|---|---|---|---|---|
| 4,690,006 A | * | 9/1987 | Urata | 73/866.5 |
| 4,855,677 A | * | 8/1989 | Clark et al. | 324/238 |
| 5,446,382 A | * | 8/1995 | Flora | 324/232 |
| 6,037,767 A | | 3/2000 | Crescenzo et al. | |
| 6,917,196 B2 | * | 7/2005 | Kwun et al. | 324/240 |
| 2003/0164698 A1 | | 9/2003 | Paulson et al. | |

FOREIGN PATENT DOCUMENTS

EP   1439262 A2   7/2004

(Continued)

OTHER PUBLICATIONS

WPI/Derwent English language abstract of FR2239173.

(Continued)

*Primary Examiner*—Jay M Patidar
(74) *Attorney, Agent, or Firm*—William H. Holt

(57) ABSTRACT

A flexible elongate structure, such as a flexible riser (10) for connecting oil and gas wells to floating production platforms, comprising at least one layer (20) of steel wires near the surface which extend at least partly along the length of the structure, can be monitored by inducing a magnetic field in the steel wires using an electromagnetic coil, and monitoring the magnetic flux density near the surface of the structure so as to detect if any wires have broken. Measurements are made at two different frequencies, the lower frequency giving an output dependent both on stresses and on the number of adjacent wires in the layer (20), and the higher frequency giving an output primarily dependent on the number of these wires. By comparing these two measurements a corrected output parameter (P) may be obtained that is indicative only of stress. A break in a wire can be expected to change the stress in that and adjacent wires.

11 Claims, 3 Drawing Sheets

| | FOREIGN PATENT DOCUMENTS | | |
|---|---|---|---|
| GB | 2140564 A | 11/1984 |
| GB | 2250097 A | 5/1992 |
| GB | 2278450 A | 11/1994 |
| JP | 62071854 A | * | 4/1987 |
| WO | 98/48269 A1 | 10/1998 |
| WO | 03/034054 A2 | 4/2003 |
| WO | 2005/001466 A1 | 1/2005 |

OTHER PUBLICATIONS

Patent Abstracts of Japan English language abstract of JP 61164151.
WPI/Derwent English language abstract of JP2000055888.

* cited by examiner

DETECTING FAILURES IN FLEXIBLE MULTISTRAND STEEL STRUCTURES

This invention relates to a method and apparatus for monitoring flexible multistrand steel structures such as cables, hoses or risers, for detecting failures.

Flexible risers are used to connect oil and gas wells to floating production platforms, the flexible riser being a steel-wire-reinforced flexible hose. Typically such a riser is connected to a turret on the floating platform, the turret providing some degree of rotation, and the flexible riser is typically hundreds or thousands of meters long. Failure in such a flexible riser can lead to significant quantities of oil leaking into the environment. It has been found that such risers typically fail close to the point at which the riser is connected to the turret, or to a support point along its length, this failure being due to the fatigue loading endured by the riser at the point where the forces are greatest due to wave motion and rotation of the floating platform. This failure mode is recognised, but there exists no technology capable of inspection of such risers to warn of catastrophic failure, particularly with the flexible riser in situ connected to the turret and carrying a product.

An electromagnetic probe may be used to detect stress in the reinforcing wires or ligaments, but the measurements are complicated by the gaps between adjacent ligaments, which are typically not uniform and may vary during use.

According to present invention various provided a method for monitoring a flexible elongate structure with a generally cylindrical surface, the structure comprising at least one layer of steel ligaments near the cylindrical surface, the steel ligaments extending at least partly along the length of the structure, the method comprising inducing an alternating magnetic field less than saturation in the steel ligaments using an electromagnet with spaced-apart poles adjacent to the cylindrical surface and monitoring the alternating magnetic flux density near the said cylindrical surface in the vicinity of the said electromagnet, from the detected flux density determining a parameter sensitive to stress in the ligaments, and from any variation of the said parameter as measured adjacent to different ligaments detecting if any ligamentous have broken or are over-stressed, wherein the alternating magnetic field is induced at at least two different frequencies at every measurement location, and the said parameter is determined from the values of flux density detected at those different frequencies.

Preferably a lower frequency is selected so as to a provide a skin depth in the steel that is between an eighth of and twice the thickness of a wire or ligament. More preferably a lower frequency provides a skin depth substantially equal to a quarter of the thickness of a wire or ligament. Preferably a higher frequency is between 2 and 8 times greater than a lower frequency, more preferably between 3 and 5 times greater, and most preferably about 4 times greater; this latter case provides a skin depth half the previous value.

Measurements taken at different frequencies enable variations in the number of wires or ligaments in the vicinity of a probe to be distinguished from variations in the stress in the wires or ligaments. Measurements may be taken adjacent to different ligaments either by using an array of such probes adjacent to different ligaments, or using a single such probe and scanning it circumferentially or longitudinally so that it passes adjacent to the ligaments in succession.

Preferably the magnetic field is in a direction that is not parallel to the longitudinal axes of the ligaments. With some steels, in which longitudinal stress has a significant effect of the transverse magnetic permeability, the magnetic field is preferably in a direction perpendicular to the ligaments; with other steels the magnetic field is preferably in a direction between 30° and 60°, more preferably about 45°, to the direction of the ligaments. The magnetic field should be less than 0.9 times the value required for saturation, preferably less than 0.5 times and more preferably less than 0.2 times, for example 0.15 or 0.10 times that value.

Flexible risers include a helically-wound steel wire layer to provide tensile strength near the outer surface of the riser, and may in fact include two such steel wire layers. The failure mode typically involves fatigue fracture of one of the outer steel reinforcing wires or ligaments. When a wire fails in this way, the remaining intact wires must take the extra load, and therefore their total stress increases. By arranging an array of electromagnetic stress sensing probes around the circumference of the riser or scanning such a probe around the circumference, the failure of one or more wires or ligaments will result in a variation of the measured stress around the circumference. An increase in stress in one region indicates the failure of a ligament in a nearby region, or at least an impending failure where a fatigue crack has propagated through a significant proportion of the cross-section of a ligament.

The preferred stress-measurement method involves resolving signals from the sensor that monitors the alternating magnetic flux density into an in-phase component and a quadrature component; and hence deducing a stress-dependent parameter which is substantially unaffected by lift-off. This requires a preliminary calibration, with a specimen of the material, to determine how the in-phase and quadrature components of the signal vary with lift-off (at a constant stress). For example the stress-dependent parameter may be calculated by resolving the signals from the sensor in a direction orthogonal to the lift-off line in the impedance plane.

Preferably the measurements are made using an electromagnetic probe incorporating an electromagnet coil to induce the alternating magnetic field, the coil being wound onto an electromagnet core, the probe also incorporating one or more sensors to monitor the magnetic flux density near the cylindrical surface. One such magnetic sensor may be arranged to sense the reluctance (or flux-linkage) of that part of the magnetic circuit between the poles of the electromagnet. Alternatively the magnetic sensor may be a flux-leakage sensor between the poles arranged to sense magnetic flux density just above the cylindrical surface in a direction parallel to the free space magnetic field. This second sensor detects flux leakage, which is influenced by changes in material properties, lift-off, and cracks. Another type of sensor has its axis perpendicular to the surface of the riser (or other structure), and may be a flat coil such as a pancake winding. This type of sensor detects components of leakage flux in radial directions, giving signals of opposite polarity at each side of a ligament, and so enables the positions of the ligaments or wires to be detected, but surprisingly its signals are also dependent on stress.

Thus the method enables failure or over-stressing of a ligament or wire to be detected, and also provides some spatial resolution as to the location of the failure. Greater resolution can be obtained by using smaller probes, but smaller probes are more affected by lift-off from the surface. A preferred arrangement uses probes that are of width between 30 mm and 90 mm, preferably about 60 mm, as such probes are not excessively affected by lift-off and nevertheless provide adequate spatial resolution. When dealing with risers, the probe may be separated from the outermost ligaments by a considerable thickness of non-magnetic material (for example a polymer layer), and in this case a larger probe provides a greater signal to noise ratio, that is to say the signal variations arising from changes in stress are proportionately larger. However a larger probe, if monitoring flux linkage, will monitor a larger number of ligaments, so the sensitivity to a break of a single ligament is reduced. Hence in this context there may be benefits from using a larger probe, for example of width up to say 150 mm, for example 110 mm wide. It will also be appreciated that the face of the probe against the surface may be of any convenient shape, for example square or rectangular. Indeed, it may be feasible to operate with an electromagnet whose poles are separated by up to half the circumference of the riser. Particularly with a large electromagnet it may be appropriate to use flux leakage or pancake sensors, rather than flux linkage sensors, as these can be small enough to provide the necessary resolution.

The flux measurement signal from the or each probe may be backed-off, i.e. processed by first subtracting a signal equal to the signal from that sensor with the probe adjacent to a stress-free location. The backed-off signal is then amplified so the small changes due to stress are easier to detect. This backing off is performed after resolving into in-phase and quadrature components but before deducing the stress-dependent parameter. Preferably the signals from the or each probe are digitized initially, and the backing-off and resolution are performed by analysis of the digital signals.

When dealing with a flexible riser, or a similar structure, the stresses in the wires or ligaments are almost exclusively along their lengths. It is also very difficult to obtain meaningful measurements by applying the alternating magnetic field parallel to the wires, because this generates eddy currents which flow around the circumference of the individual wires, which overwhelm any effect due to changes in magnetic permeability.

The invention will now be further and more particularly described, by way of example only, and with reference to the accompanying drawings, in which.

Figure 1:
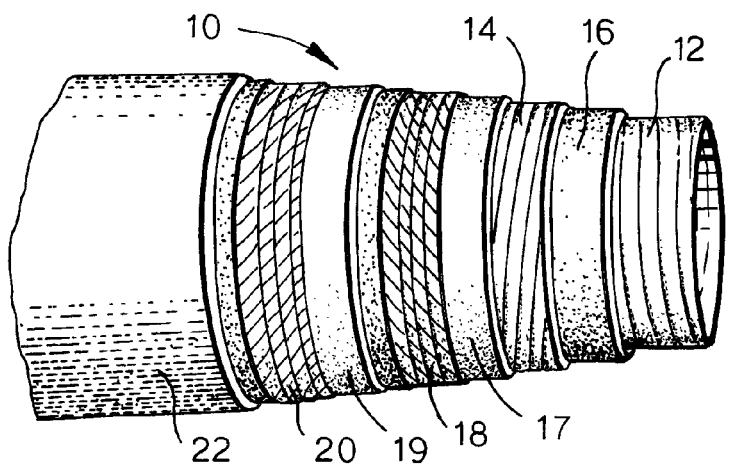
FIG. 1 shows a perspective cut-away view of part of a riser, to show its internal structure.

Referring to FIG. 1, a flexible riser 10, which acts as a hose to carry a pressurised fluid, has several concentric layers. An innermost layer 12 of helically wound bent steel strip provides resistance against external pressures, and a similar helically wound steel strip layer 14 provides hoop strength, and between these layers is a fluid barrier layer 16 of polymeric material. These are surrounded by two layers 18 and 20 of helically-wound steel ligaments or wires to provide tensile strength, separated from the steel strip layer 14 and from each other by respective anti-wear layers 17 and 19. A polymeric layer 22 provides an external sleeve and fluid barrier. As discussed above, the failure mode with such a riser 10 is typically the failure of one or more ligaments in the outermost layer 20. But it will be appreciated that these ligaments cannot be observed directly, because they are enclosed within the outer layer 22.

Figure 2:
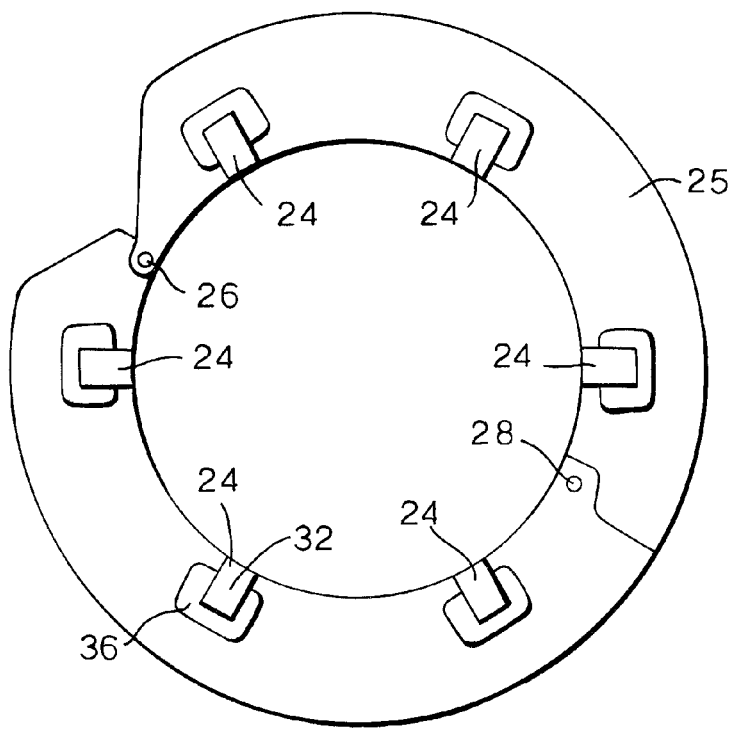
FIG. 2 shows an end view of a probe array for monitoring a riser as shown in FIG. 1, by making measurements of stress.

Referring now to FIG. 2, the stresses in the outermost layer 20 of steel ligaments of a riser 10 as shown in FIG. 1 may be monitored using an array of electromagnetic stress-measuring probes 24 in an annular frame 25. The frame 25 is in two generally semicircular halves which are hinged together at a pivot pin 26 and locked into an annular form by a securing pin 28. Hence in use the frame 25 can be clamped so as to surround the riser 10, there being a clearance of no more than 2 mm between the inside of the frame 25 and the outer surface of the riser 10. The frame 25 is shown as carrying only six electromagnetic probes 24, although it will be appreciated that it might support a different number, and indeed it would be preferable to have the separation between adjacent probes 24 similar to the width of each probe 24. (If probes are close to each other, they should not be energised at the same time.) If greater spatial resolution is required, there might be a second such array of probes 24 axially displaced and staggered in position relative to those shown.

Alternatively the stresses might be monitored using a single such probe 24 that is scanned around the circumference, measurements being taken at a multiplicity of successive locations.

Figure 3:
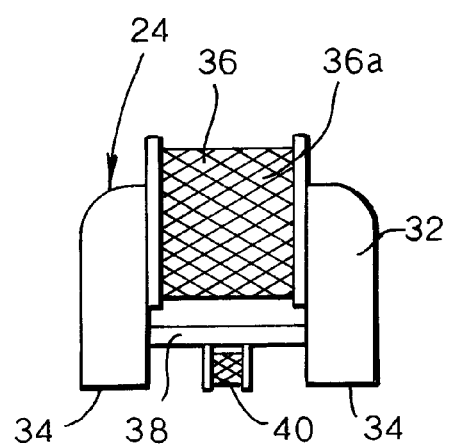
FIG. 3 shows a longitudinal sectional view of a probe for use in the array of FIG. 2.

Referring now to FIG. 3, each probe 24 includes a U-core 32 of silicon iron which defines two rectangular poles 34 in a common plane, each pole being 60 mm by 12 mm, and the space between the poles being 60 mm by 36 mm. The faces of the poles 34 are slightly curved to match the curvature of the outer surface of the riser 10. Around the upper end of the U-core 32 is a former on which are wound two superimposed coils 36 and 36a. One coil 36 has 145 turns, and in use is supplied with an AC current of 0.6 A; this is the energising coil 36. When energized, this generates an alternating magnetic field in the U-core 32 and in the adjacent helically-wound steel ligaments of the layer 20 in the riser 10, this magnetic field being small compared to the saturation field for the steel. The orientation of the probes 24 is such that the free space magnetic field is in a direction at 90° to the orientation of the steel ligaments in the layer 20. The other coil 36a is a sensing coil which provides the reluctance signals.

The probes 24 may also include other magnetic sensors, for example there may be a coil 40 between the poles whose longitudinal axis is parallel to the free-space magnetic field direction, supported on a non-magnetic plate 38 fixed between the arms of the U-core 32. This coil 40 detects leakage flux. The signals from the sensing coil 36a and from the leakage flux coil 40 (if provided) are amplified by a head amplifier before further processing.

In operation, with the probes 24 clamped around the riser 10, the alternating current is supplied to the drive coils 36. The in-phase and quadrature components of the flux linkage signal (i.e. the component in phase with the drive current, and the component differing in phase by 90°) received from the sensing coil 36a are each backed off to zero, and the backing off values are then fixed. During all subsequent measurements the flux linkage components are backed off by these same amounts (i.e. subtracting a signal equal to the component observed at a stress-free location or at any rate a location of uniform stress). Preferably the signals are digitised before backing off.

A parameter indicative of the stress in the layer 20 in the longitudinal direction can be determined from the experimental measurements of flux linkage, once the measurements have been compensated for lift-off. This requires calibration of the probe 24. As explained in WO 03/034054, such a compensation may be carried out graphically, the backed-off in-phase and quadrature components of the reluctance signal from the coil 36a being plotted on a graph, measurements being obtained first with varying lift-off and then with varying stress. Alternatively such corrections may be carried out algebraically for example as described in WO 2005/001466. However in the present situation it is only necessary to compensate for any changes in lift-off, and this can be achieved by a calibration using one such probe 24, taking measurements at progressively larger values of lift-off from the surface of the riser 10. This gives a changing-lift-off contour in the impedance plane.

Subsequently, measurements can be compensated for lift-off by determining the component in the direction orthogonal (in the impedance plane) to the direction of the changing-lift-off contour. This orthogonal component is the output parameter, and is dependent upon stress.

In this example the ligaments in the layer 20 are rectangular in cross-section, each 4 mm thick and 12 mm wide. Measurements are made with each probe 24 in the array (or with a single probe 24 that is scanned around the circumference), at any one position measurements being taken at 70 Hz and then at 280 Hz. These measurements might for example be taken successively within 1 s of each other (so that the ligaments will not have moved between the measurements), preferably within 0.3 s of each other, for example after 0.2 s. At 70 Hz the skin depth in steel is about 1.2 mm. The value of the output parameter obtained at 70 Hz is dependent upon the stress in the wires, but is also affected by the number of wires in the immediate vicinity of the probe 24, and this number will not only vary between different locations around the circumference, but will also vary as the longitudinal stress in the riser 10 varies. At 280 Hz the skin depth is only about 0.6 mm, and the value of the output parameter is primarily determined by the number of ligaments in the immediate vicinity of the probe 24. By comparing the values of the output parameter at at least two different frequencies, the variations in the number of ligaments can be eliminated, so providing a corrected output parameter dependent only on the stress in the ligaments.

The two values are preferably normalised so that with unstressed (or uniformly stressed) ligaments the values are equal; then the difference between the normalised values may be taken as the corrected output value, P. The appropriate amplification for normalisation can be determined by scanning a section of riser at the one frequency, and then at the other; this produces signals which display peaks and troughs (caused by the geometrical arrangement of the ligaments), and the two signals are scaled so that they have equal ranges between peaks and troughs, that is to say equal sensitivity to ligament separations; they may also be adjusted so that the signals in each case range between the same values (say 0 and 1). In the latter case, the ratio between the two normalised values of the output parameter at these two different frequencies might instead be taken as the output value.

Figure 4:
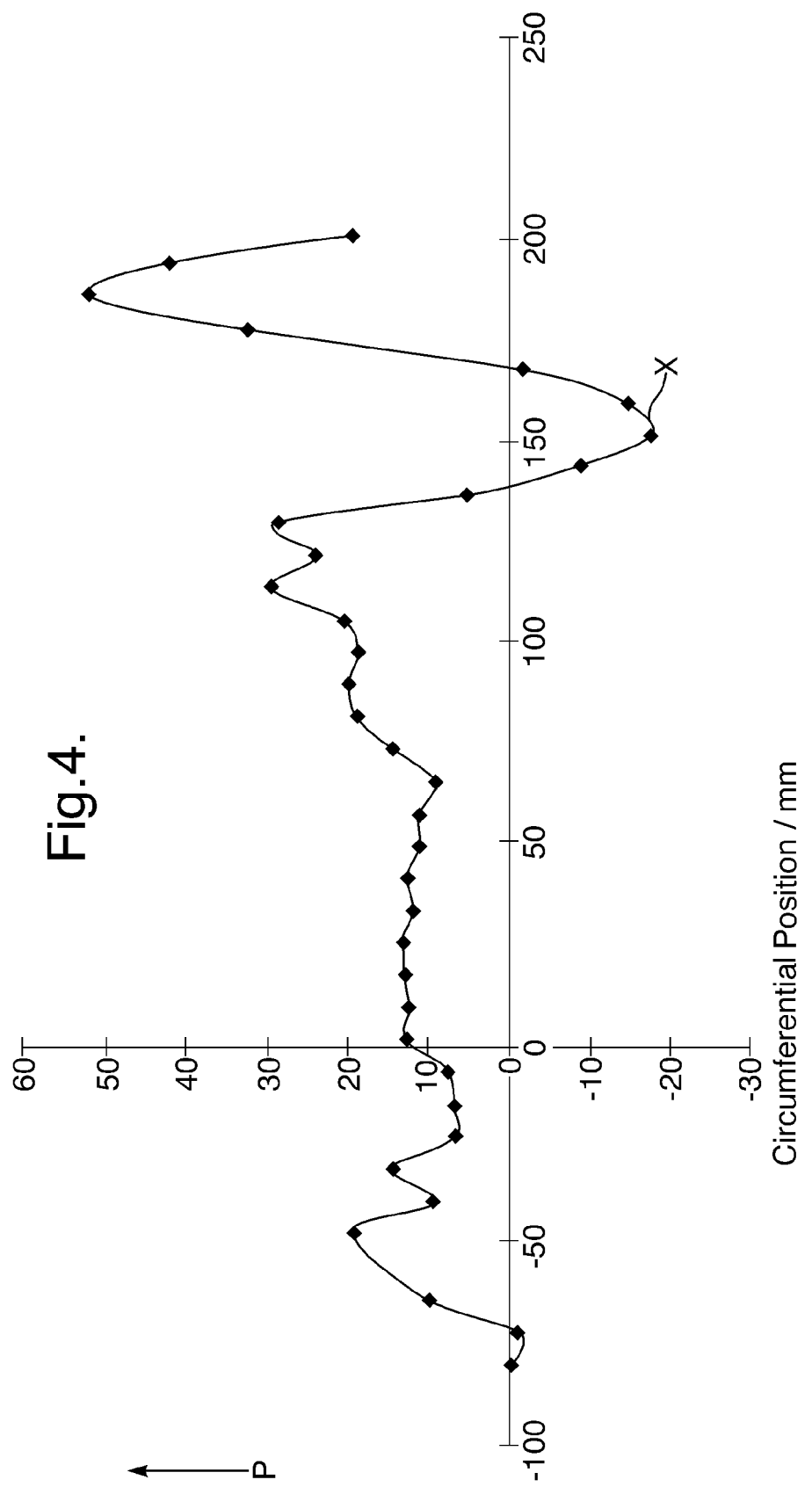
FIG. 4 shows graphically measurements made on a riser as shown in FIG. 1 using a probe as shown in FIG. 3, in which a broken wire is evident.

Referring now to FIG. 4 there is shown graphically the corrected output parameter P obtained in this way using a single probe 24 scanned around the circumference of a riser 10, in which one ligament had been cut, in an experimental setup in which the riser 10 was subjected to internal hydrostatic pressure so that the ligaments are under longitudinal stress. In this case the signals had been normalised with an unstressed riser, and the output parameter P is the difference between the normalised values. It can be seen that for most of the circumference the output parameter is small and positive (indicating the longitudinal stress), but at the position marked X one of the ligaments is clearly under a markedly smaller stress than the others. This is indicative of there being a cut in that ligament.

Referring now to FIG. 5 the experimental results are shown for measurements made scanning a single probe longitudinally along a section of riser subjected to a longitudinal stress, in which three adjacent ligaments in the outer layer were cut at a position 103 mm from the end. Measurements were made using three different sensor coils: a flux linkage sensing coil 36a, a flux leakage-sensing coil 40, and a flat "pancake" coil (not shown) whose axis is perpendicular to the surface of the riser 10. In each case the probe was arranged with the magnetic field direction approximately at right angles to the orientation of the ligaments in the outer layer, and the signals measured at each frequency, after being corrected for liftoff as described above, were normalised to provide equal values for ligament separation sensitivity, and the difference between the normalised signals at the two frequencies was taken as the stress parameter, P. The measurements were taken as the probe was scanned along the section of riser, starting at about 700 mm and ending up at about 3800 mm from the end. Because the ligaments are wound helically, the probe crosses over the cut ligaments at intervals of about 880 mm.

Figure 5A:
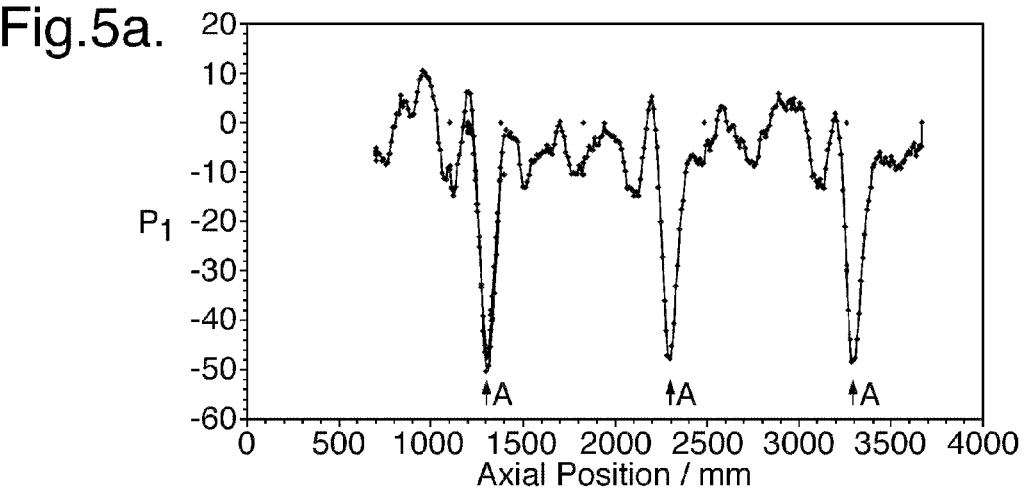
FIGS. 5a to 5c show measurements made with a probe as shown in FIG. 3, but with three different types of sensor.

FIG. 5a shows the variation in the stress parameter P1 measured using the flux linkage sensing coil 36a. It will be observed that the stress parameter P1 provides a large negative signal on the three occasions that the probe passes over the cut ligaments. The magnitude of the peak decreases slightly between the first and second occasions that the probe passes over the ligaments, but it is clear that even at a distance of over 3 m from the position of the cut, the peak indicating decreased stress is clearly distinguishable from the background variation between other ligaments.

Figure 5B:
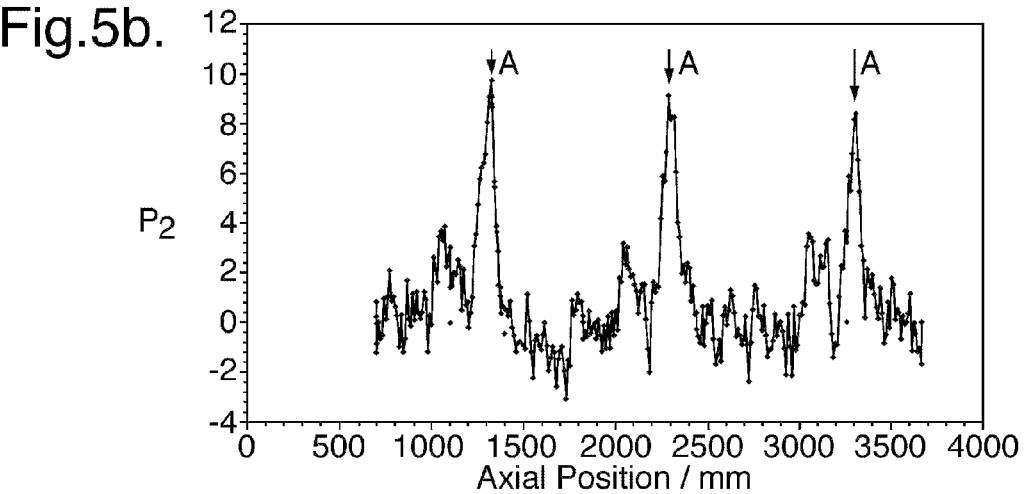

FIG. 5b shows the variation in the stress parameter P2 measured using the flux leakage sensing coil 40. In this case the stress parameter P2 provides a large positive signal whenever the probe passes over the ligaments that had been cut. The magnitude of the peak decreases with distance from the position of the cut.

Figure 5C:
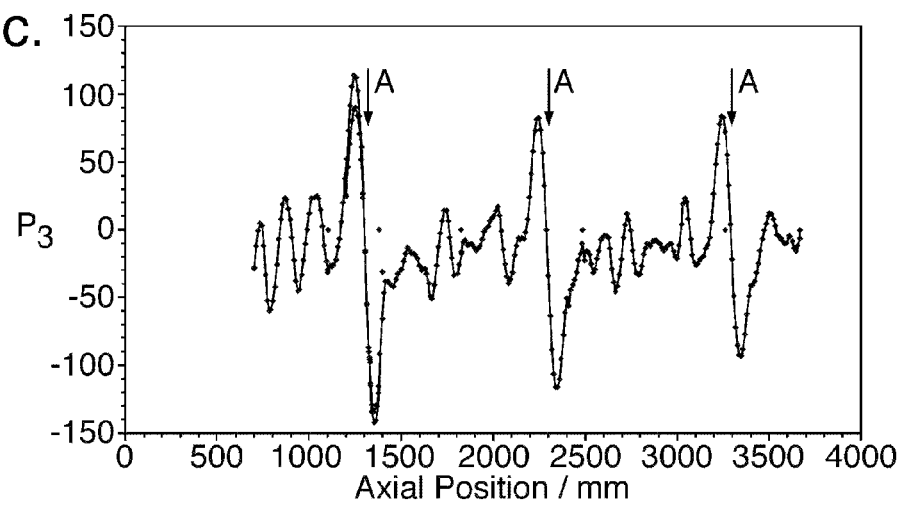

FIG. 5c shows the variation in the stress parameter P3 measured using the flat "pancake" coil. In this case the stress parameter P3 is zero as the probe is directly above the ligaments that have been cut, but provides a large positive signal just before the cut ligaments and a large negative signal just after the cut ligaments. Again the magnitude of the peaks decreases slightly with distance from the position of the cut, but as with the other sensors, the peak is clearly distinguishable from background variations even at over 3 m from the position of the cut. These measurements suggest that the cut ligaments could be detected at a distance of some metees, possibly as far as 10 m.

With a riser 10, a break in a ligament within the outer layer 20 locally reduces the stress in that ligament to near zero and slightly increases the stresses in all the other ligaments. Over a length of several metees the resulting non-uniformities in stress even out, as stresses are transmitted between adjacent ligaments. However, it has been found that such a break in a steel ligament almost always occurs near an end of the riser 10, within the connection to an end-fitting. Hence as long as the probe 24 (or the array of probes 24) is arranged to monitor stresses within a few meters of an end of the riser, the ligament failure can be detected from the consequential stress differences. The measurements are preferably made no more than 6 m from the end-fitting, and more preferably no more than 4 m from the end-fitting.

From the description above it will be appreciated that when inspecting a riser that incorporates smaller wires or ligaments, it would be appropriate to use higher frequencies, so that the skin depth is matched to the size of the wires. For example if the riser contained an outer layer of wires of diameter 2 mm, then suitable frequencies would be four times greater, i.e. 280 Hz and 1120 Hz. It will also be appreciated that these frequencies are given by way of example only, and that the inspection might use somewhat different frequencies, for example 250 Hz and 1200 Hz, as the higher frequency might be a different multiple of the lower frequency.

An inspection apparatus as described in relation to FIG. 2 might for example be installed on a riser in the vicinity of an end-fitting to monitor for any breaks in the ligaments, and may be installed temporarily (to carry out occasional inspections) or permanently. Alternatively it might be scanned along the length of a hose or riser, so that failure of wires along the entire length can be detected; if a localised area of increased stress is detected, this may be due to a failure in the inner hoop windings 12.

The invention claimed is:

1. A method for monitoring a flexible elongate structure with a generally cylindrical surface, the structure comprising at least one layer of steel ligaments near the cylindrical surface, the steel ligaments extending at least partly along the length of the structure, the method comprising inducing an alternating magnetic field less than saturation in the steel ligaments using an electromagnet with spaced-apart poles adjacent to the cylindrical surface, and monitoring the alternating magnetic flux density near the said cylindrical surface in the vicinity of the said electromagnet, from the detected flux density determining a parameter sensitive to stress in the ligaments, and from any variation of the said parameter as measured adjacent to different ligaments detecting if any ligaments have broken, wherein the alternating magnetic field is induced at least two different frequencies at every measurement location, and the said parameter is determined from the values of flux density detected at those different frequencies.

2. A method as claimed in claim 1 wherein a lower frequency is selected so as to a provide a skin depth in the steel of the ligaments that is between an eighth of and twice the thickness of a ligament.

3. A method as claimed in claim 2 wherein the lower frequency provides a skin depth substantially equal to a quarter of the thickness of a ligament.

4. A method as claimed in claim 1 wherein a higher frequency is at least twice a lower frequency.

5. A method as claimed in claim 4 wherein the higher frequency is between 3 and 5 times greater than the lower frequency.

6. A method as claimed in claim 1 wherein the magnetic field is in a direction that is not parallel to the longitudinal axes of the ligaments.

7. A method as claimed in claim 1 wherein the measurements are made using an electromagnetic probe incorporating an electromagnet coil to induce the alternating magnetic field, the coil being wound onto an electromagnet core, the probe also incorporating one or more sensors to monitor the magnetic flux density near the cylindrical surface.

8. A method as claimed in claim 7 wherein signals from the sensor that monitors the alternating magnetic flux density are resolved into an in-phase component and a quadrature component, from which the stress-dependent parameter is determined such that the stress-dependent parameter is substantially unaffected by lift-off.

9. A method as claimed in claim 8 wherein the stress-dependent parameter is calculated by resolving the signals from the sensor in a direction orthogonal to the lift-off line in the impedance plane at each of the frequencies, and comparing the resolved signals.

10. A method as claimed in claim 9 wherein the resolved signals are normalised, and then the difference between the normalised values is taken as the stress-dependent parameter.

11. A method as claimed in claim 1, the method using an array of probes in an annular support frame around the circumference of said flexible elongate structure.

* * * * *